(12) United States Patent
Bennett et al.

(10) Patent No.: US 8,927,267 B2
(45) Date of Patent: Jan. 6, 2015

(54) CELL VISUALIZATION SYSTEM FOR MULTI-LAYER CELL CULTURE DEVICE

(75) Inventors: Scott Matthew Bennett, Gorham, ME (US); David Alan Kenney, Chelmsford, MA (US); Gregory Roger Martin, Acton, ME (US); Jeffry J Santman, Westmoreland, NH (US); Allison Jean Tanner, Portsmouth, NH (US)

(73) Assignee: Corning Incorporated, Corning, NY (US)

( * ) Notice: Subject to any disclaimer, the term of this patent is extended or adjusted under 35 U.S.C. 154(b) by 770 days.

(21) Appl. No.: 13/235,952

(22) Filed: Sep. 19, 2011

(65) Prior Publication Data

US 2012/0070887 A1 Mar. 22, 2012

Related U.S. Application Data

(60) Provisional application No. 61/385,542, filed on Sep. 22, 2010.

(51) Int. Cl.
| | |
|---|---|
| *C12M 1/12* | (2006.01) |
| *C12M 3/00* | (2006.01) |
| *C12M 1/18* | (2006.01) |
| *C12M 1/04* | (2006.01) |
| *C12M 1/34* | (2006.01) |
| *C12M 1/00* | (2006.01) |

(52) U.S. Cl.
CPC ............... *C12M 25/06* (2013.01); *C12M 25/02* (2013.01); *C12M 23/22* (2013.01); *C12M 23/24* (2013.01); *C12M 41/36* (2013.01)
USPC .................. 435/297.5; 435/289.1; 435/292.1; 435/294.1; 435/295.3; 435/297.1

(58) Field of Classification Search
None
See application file for complete search history.

(56) References Cited

U.S. PATENT DOCUMENTS

| | | | |
|---|---|---|---|
| 4,734,373 | A | 3/1988 | Bartal et al. |
| 4,979,332 | A | 12/1990 | Nagaya et al. |
| 6,238,911 | B1 | 5/2001 | Kasahara |
| 2007/0026516 | A1 | 2/2007 | Martin et al. |
| 2009/0191620 | A1 | 7/2009 | Martin et al. |

FOREIGN PATENT DOCUMENTS

| | | |
|---|---|---|
| JP | 2005/245288 | 9/2005 |
| JP | 2005/333912 | 12/2005 |
| WO | 2007/043561 | 4/2007 |
| WO | 2008/073313 | 6/2008 |

*Primary Examiner* — Neil N Turk
(74) *Attorney, Agent, or Firm* — Susan S. Wilks

(57) ABSTRACT

The present invention relates generally to a multi-layer system for containing cells in culture, and a system for visualizing cells cultured in the multi-layered system. More specifically, the present invention relates to a multi-layer cell culture device having a specialized bottom plate and a microscope adaptor which can accommodate a microscope to allow microscopic visualization of cells cultured in the device.

17 Claims, 7 Drawing Sheets

CELL VISUALIZATION SYSTEM FOR MULTI-LAYER CELL CULTURE DEVICE

CROSS-REFERENCE

This application claims the benefit of priority under 35 U.S.C. §119 of U.S. Provisional Application Ser. No. 61/385,542 filed on Sep. 22, 2010 the content of which is relied upon and incorporated herein by reference in its entirety.

FIELD

The present invention relates generally to a system for visualizing cells cultured in multi-layered cell culture devices. More specifically, the present invention relates to a multi-layer cell culture device having a specialized bottom plate and a microscope adaptor which can accommodate a microscope lens to allow microscopic visualization of cells cultured in the device.

BACKGROUND

Cells are cultured in specialized cell culture containers including roller bottles, cell culture dishes and plates, multi-well plates, microtiter plates, common flasks and multi-layered cell growth flasks and vessels. Cells in culture attach to and grow on the bottom surface(s) of the flask, immersed in a suitable sustaining media.

Traditional cell culture vessels are constructed with a large internal space ("headspace") devoted to gas exchange. This headspace creates a requirement for laboratories growing cells in culture to use inverted microscopes to enable cell visualization. The extended optical pathway through a large body of air inside traditional cell culture vessels precludes the use of standard upright microscopes to visualize the cells growing within the traditional vessel. Most cell culture laboratories utilize inverted microscopes to visualize cells in culture.

With the advent of cell-based high-throughput applications, cell culture vessels or devices have been developed to provide an increased surface area for cell growth while also providing necessary gas exchange. These systems also employ traditional cell culture vessels including common flasks, roller bottles, cell culture dishes, as well as multi-layered cell growth vessels including multi-layer flasks, multi-layer cell culture dishes, bioreactors, cell culture bags and the like, which may include specialized surfaces designed to enhance the cell culture parameters including growth density and differentiation factors. For example, Corning Incorporated sells multi-layer cell culture devices such as the HYPERStack® and the HYPERFlask®. See, for example, US Publication No. 2007/0026516. While such multi-layer cell culture devices enable an increased surface area for cells in culture, these multiple layers of cells in culture obstruct the visualization of cells cultured in these devices.

The configuration of multi-layer vessels is very different from traditional cell culture vessels in that the air required for cellular metabolism is obtained through spaces ("tracheal spaces") beneath each cell growth layer, where each cell growth layer has cell growth surface which is constructed from a gas permeable material. By having an essentially external headspace, the volumetric footprint of the individual cell culture compartments is more compact than those of traditional cell culture vessels. This permits the stacking of many cell culture layers together to provide more surface area than that which is available in traditional cell culture vessels of similar volumetric size. Removal of the headspace permits cell visualization on the top layer using standard upright microscopes that might have enough space between the stage and the objective lenses to position the vessel.

However, the stacking of the cell culture layers in multi-layer vessels does not permit visualization of all the cell culture layers. The design of some multi-layer vessels such as the HYPERStack even prevents visualization of the lowest cell culture layer using an inverted microscope with standard objective lenses.

There is a need for multi-layer cell culture vessels that can engage with a microscope to allow cells to be evaluated microscopically while still in culture in the device.

SUMMARY

Embodiments of the invention provide, among other things, A multi-layer cell culture device comprising at least two cell culture chambers, each cell culture chamber having a gas permeable, liquid impermeable membrane forming a bottom surface, side walls and an opposing plate forming a top surface, wherein the gas permeable, liquid impermeable membrane forming a bottom surface and the opposing plate are sealed to side walls to form cell culture chambers, wherein the opposing plate has a top side and the top side of the opposing plate has bumps, wherein each cell culture chamber is adjacent to a tracheal space; and, a bottom plate comprising a bottom side having support ribs having a depth "d" and a top side having bumps; wherein the gas permeable, liquid impermeable membrane of each cell culture chamber rests on the bumps on the top side of an opposing plate of an adjacent cell culture chamber or the bottom plate; wherein the bottom plate further comprises at least one window between support ribs; and wherein the top side of the bottom plate opposite the at least one window is free of bumps. In additional embodiments, the multi-layer cell culture device of wherein the support ribs extend from one side to an opposite side of the bottom plate. In additional embodiments, the disclosure provides a system for visualizing cells in a multi-layer cell culture device comprising the multi-layer cell culture device and further comprising a focal point length extender structured and arranged to fit into the at least one window. In embodiments, the focal point length extender comprises a lens, a double lens, and/or a block of high refractive index material. In embodiments, the focal point length extender wherein the focal point length extender is longer than the depth "d" of the support ribs.

In embodiments, the bottom plate has a lock feature. In embodiments, the lock feature is a press-lock. In embodiments, the lock feature is releasable. In additional embodiments, the lock feature is a permanent locking feature. In embodiments, the bottom plate has strap recesses, rivet holes, feet or bosses.

These and other advantages of the various embodiments of the devices and methods described herein will be readily apparent to those of skill in the art upon reading the disclosure presented herein.

BRIEF DESCRIPTION OF THE DRAWINGS

The invention is best understood from the following detailed description when read with the accompanying drawing figures.

DETAILED DESCRIPTION

In embodiments, the present disclosure provides a multi-layer cell culture device having a bottom plate structured and arranged to accommodate a microscope to allow microscopic visualization of cells cultured in the device. The disclosure includes also provides embodiments of an optical bridge or a focal point length extender to enable visualization of cells that lie in planes beyond the focal length of standard objective lenses in inverted microscopes.

Visualizing cells in culture is a standard method of evaluating cell culture. For example, by visualizing cells, it is possible to establish the level of confluence of cells growing within a cell culture vessel. Visualizing cells is required to determine whether the cells in culture exhibit the appropriate morphology. Visualizing cells in culture also permits determination of possible contaminating organisms in the culture. The inability to visualize the cells in culture on all layers in a multi-layer stacked cell culture vessels is an impediment to the adoption and use of these multi-layer vessels. Therefore, there is a need to provide devices and methods to visualize cells in culture in multi-layer cell culture devices.

In the following detailed description, for purposes of explanation and not limitation, exemplary embodiments disclosing specific details are set forth in order to provide a thorough understanding of the present invention. However, it will be apparent to one having ordinary skill in the art that the present invention may be practiced in other embodiments that depart from the specific details disclosed herein. In other instances, detailed descriptions of well-known devices and methods may be omitted so as not to obscure the description of the present invention.

Figure 1:
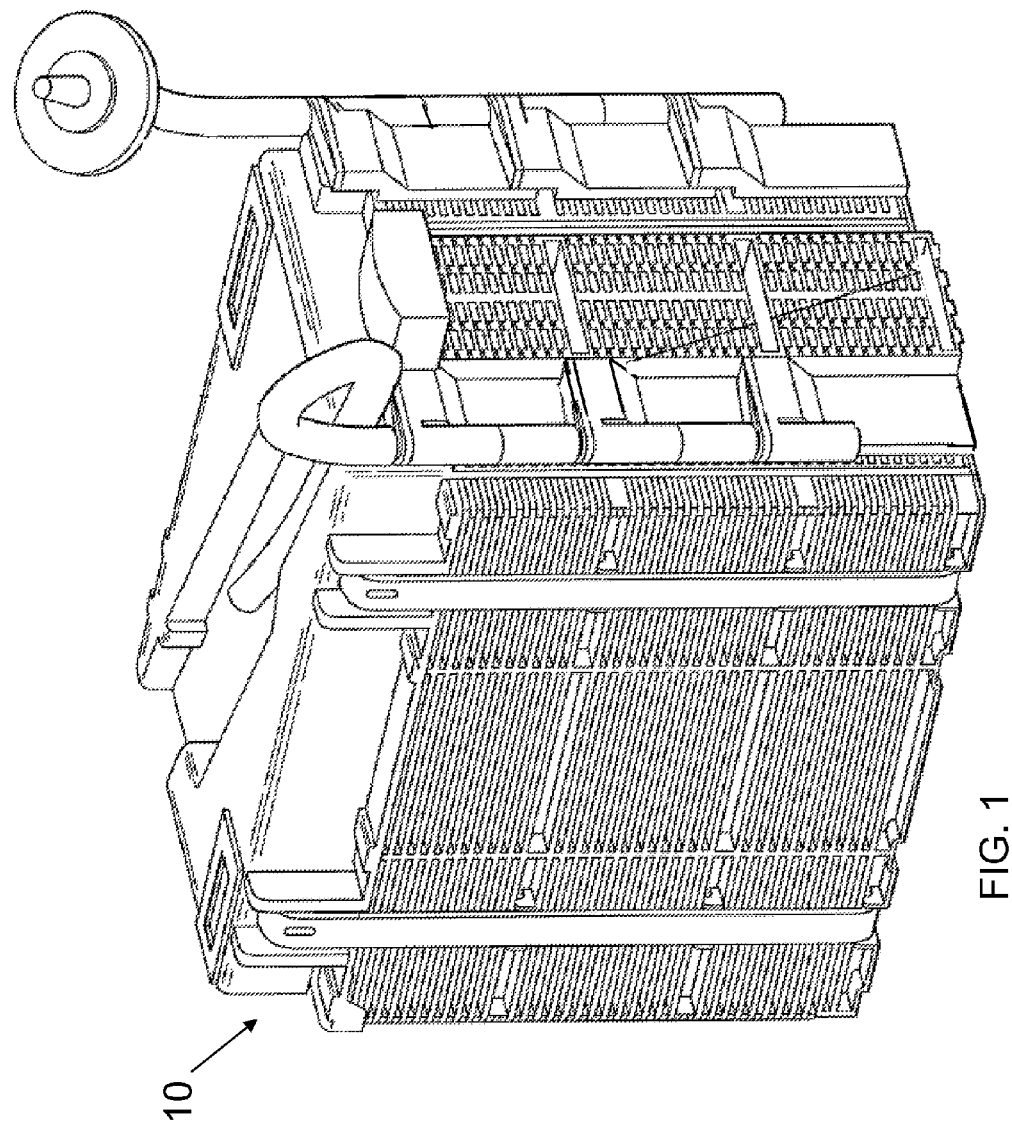
FIG. 1 is a drawing illustrating an embodiment of a multi-layer cell culture device.

FIG. 1 is a drawing illustrating an embodiment of a multi-layer cell culture device 10. The multi-layer cell culture device has at least two cell culture chambers. In the device shown in FIG. 1, there are thirty six cell culture chambers.

Figure 2:
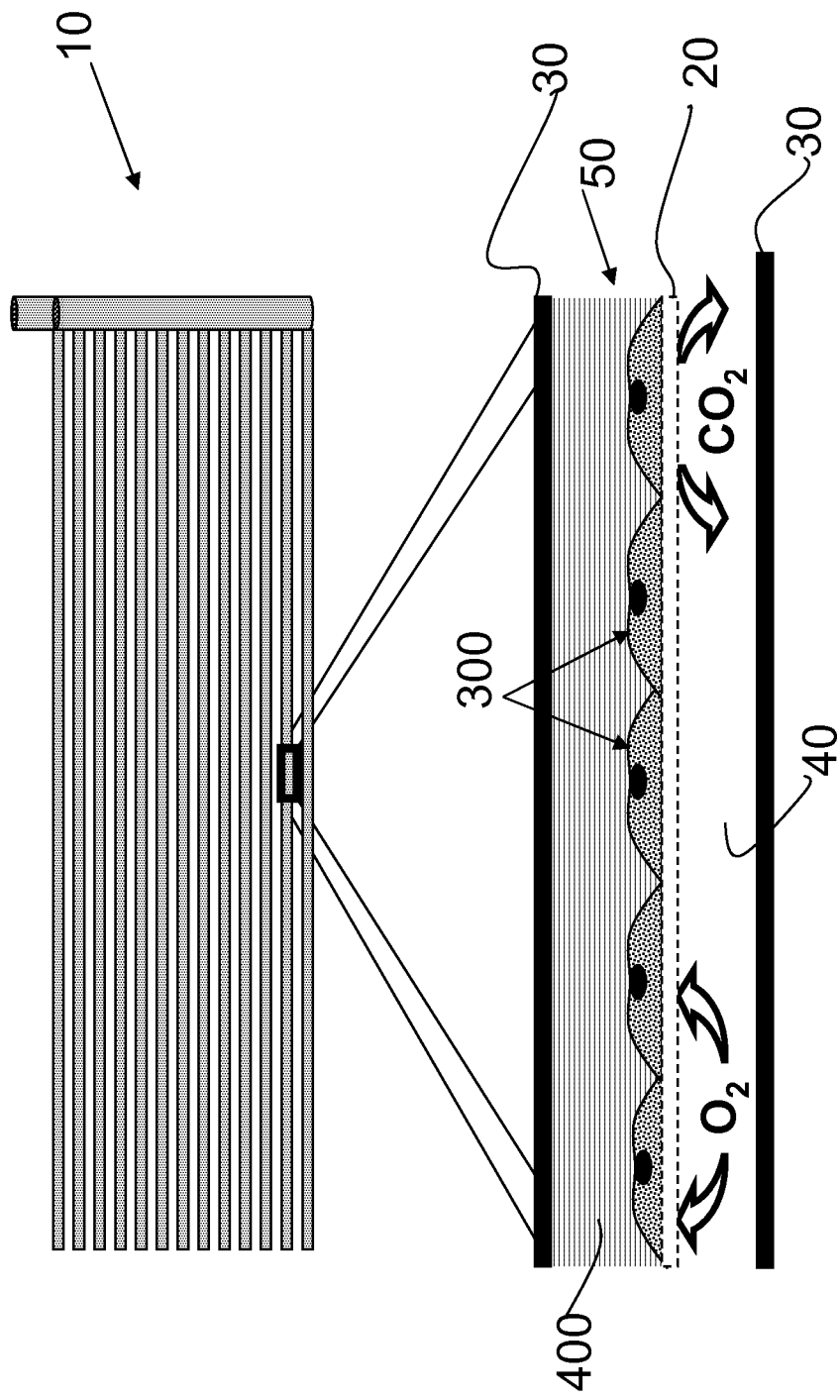
FIG. 2 is a drawing illustrating an embodiment of a layer of a multi-layer cell culture device.
Figure 5:
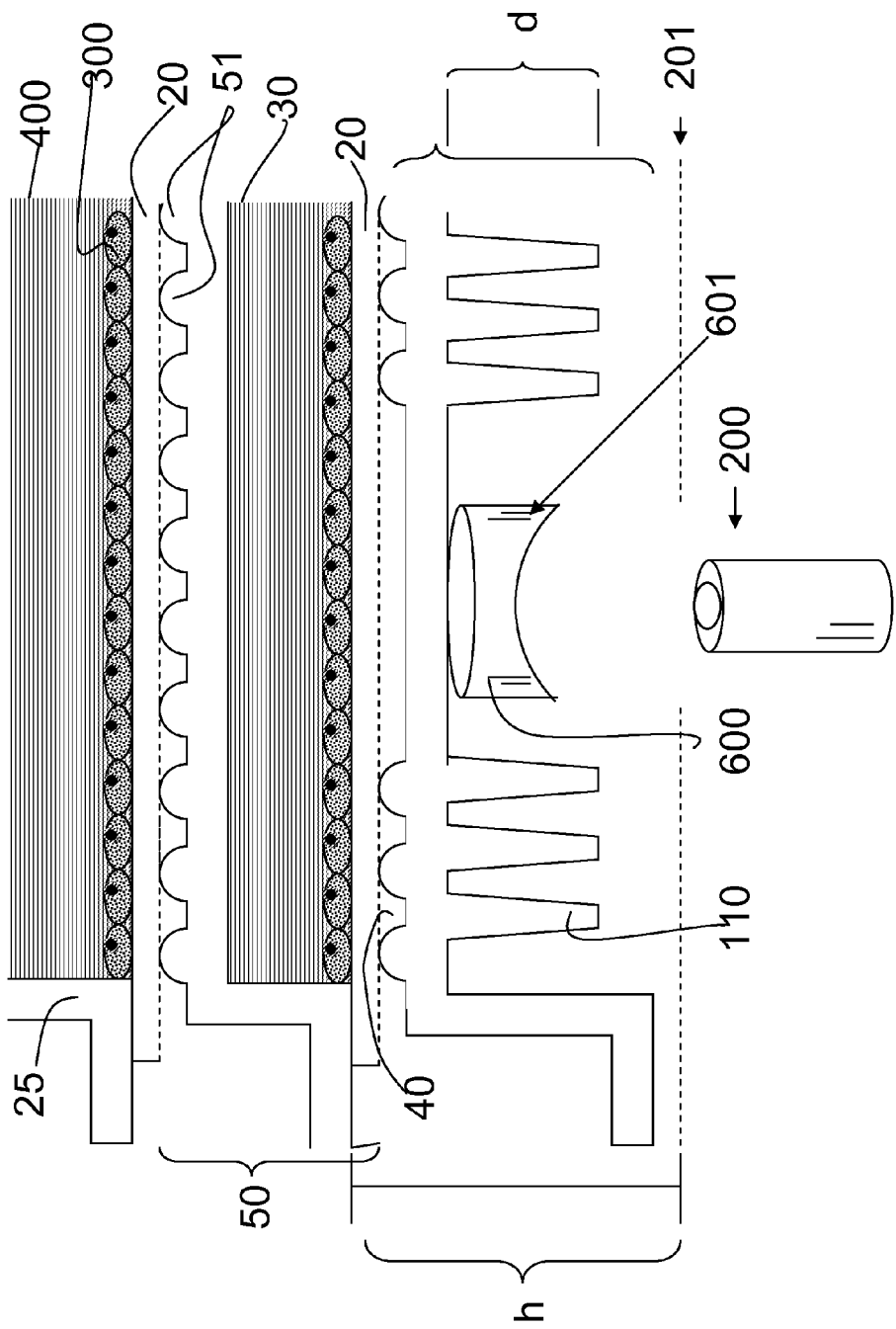
FIG. 5 is a drawing illustrating an embodiment of the bottom two cell culture layers of a multi-layer cell culture device, and an embodiment of a bottom plate, structured and arranged to accommodate a microscope lens, and also showing an embodiment of a microscope adaptor.
Figure 6:
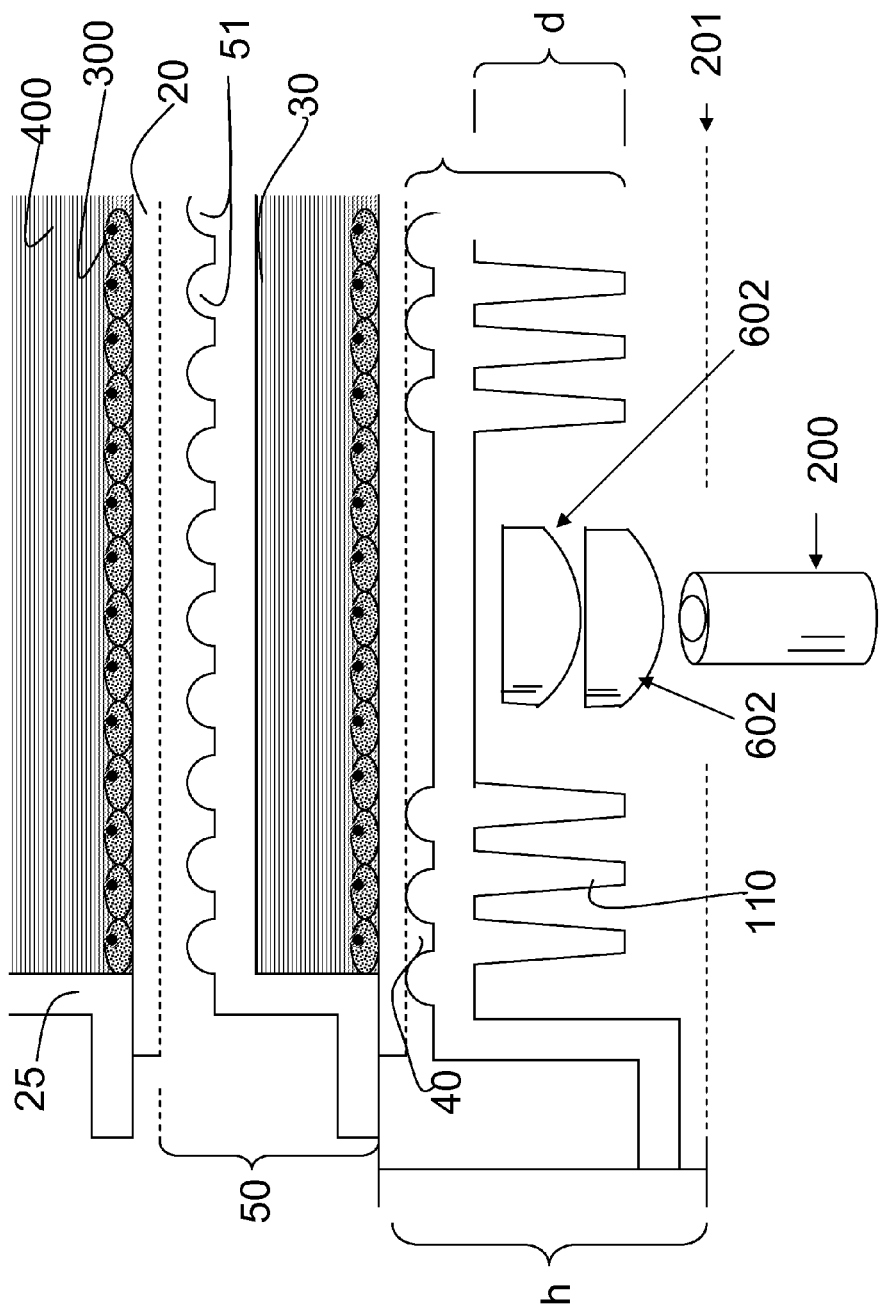
FIG. 6 is a drawing illustrating an embodiment of the bottom two cell culture layers of a multi-layer cell culture device, and an embodiment of a bottom plate, structured and arranged to accommodate a microscope lens, and also showing an embodiment of a microscope adaptor.
Figure 7:
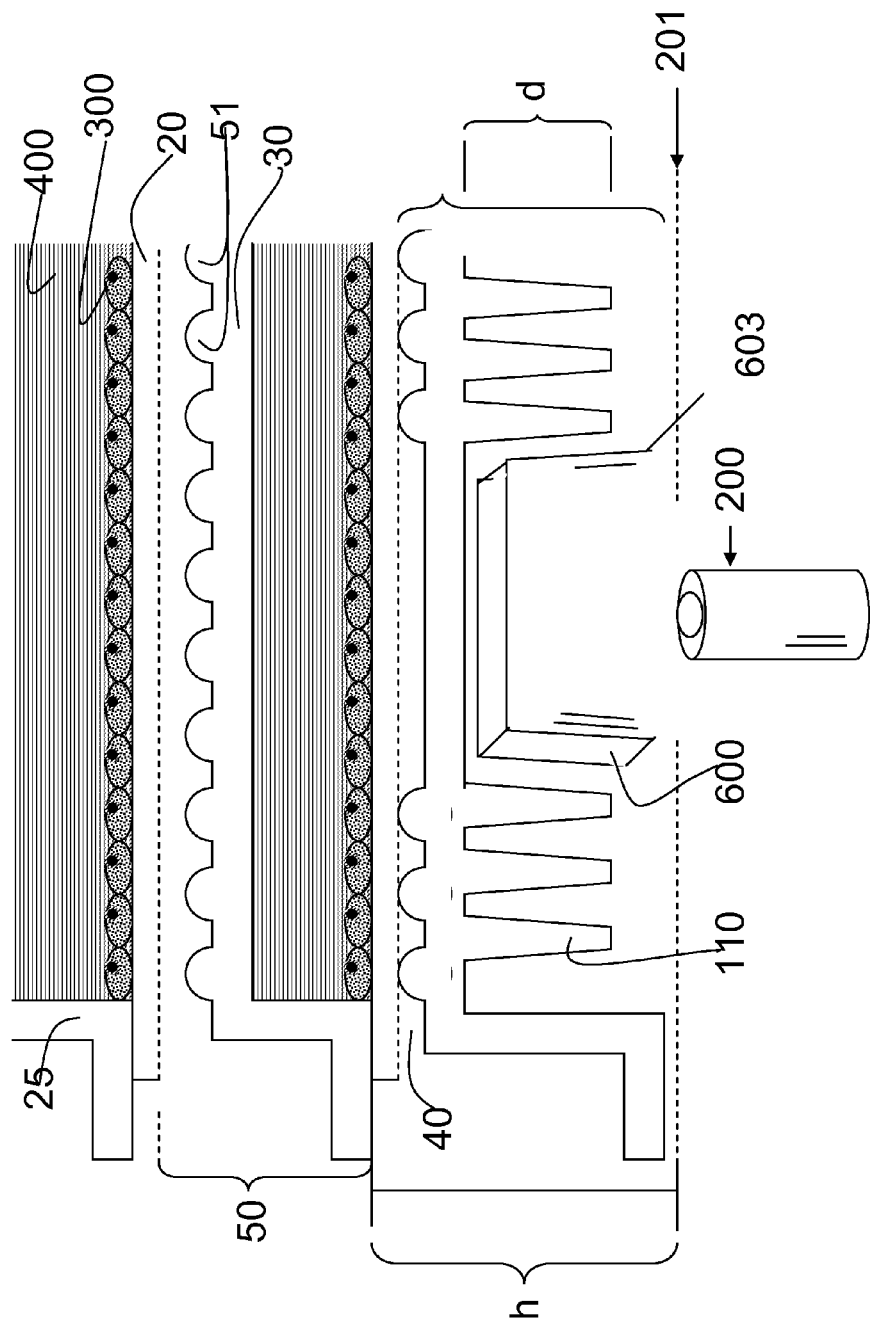
FIG. 7 is a drawing illustrating an embodiment of the bottom two cell culture layers of a multi-layer cell culture device, and an embodiment of a bottom plate, structured and arranged to accommodate a microscope lens, and also showing an embodiment of a microscope adaptor.

FIG. 2 is a drawing illustrating an example of a layer of a multi-layer cell culture device. As shown in FIG. 2, each layer has a gas permeable, liquid impermeable membrane 20 forming a bottom cell culture surface of the cell culture chamber 50. Each cell culture chamber has an opposing plate forming a top surface of a cell culture chamber 30. The gas permeable, liquid impermeable membrane 20 forming the bottom surface of the cell culture chamber and the opposing plate forming the top surface of each cell culture chamber are sealed to side walls 25 (see FIGS. 5-7), forming cell culture chambers 50. As shown in FIGS. 5-7, each opposing plate forming the top surface of each cell culture chamber has a top side, and the top side of the opposing plate has bumps 51. Each cell culture chamber is adjacent to a tracheal space 40. Tracheal spaces 40 are formed between the top surface of the opposing plate 30 and the gas permeable liquid impermeable membrane 20. The gas permeable, liquid impermeable membrane 20 rests on the bumps 51 projecting from the top surface 31 of the opposing plate 30 (see FIGS. 5-7). As shown in FIG. 2, by arrows, oxygen diffuses into the cell culture chambers from the tracheal spaces, through the gas permeable, liquid impermeable membrane, and carbon dioxide diffuses out of the cell culture chambers into the tracheal chamber, through the gas permeable, liquid impermeable membrane. Cells 300 are shown in FIG. 2 resting on the gas permeable, liquid impermeable membrane 20 forming the bottom surface of the cell culture chamber. Media 400 fills the cell culture chamber 50.

Figure 3:
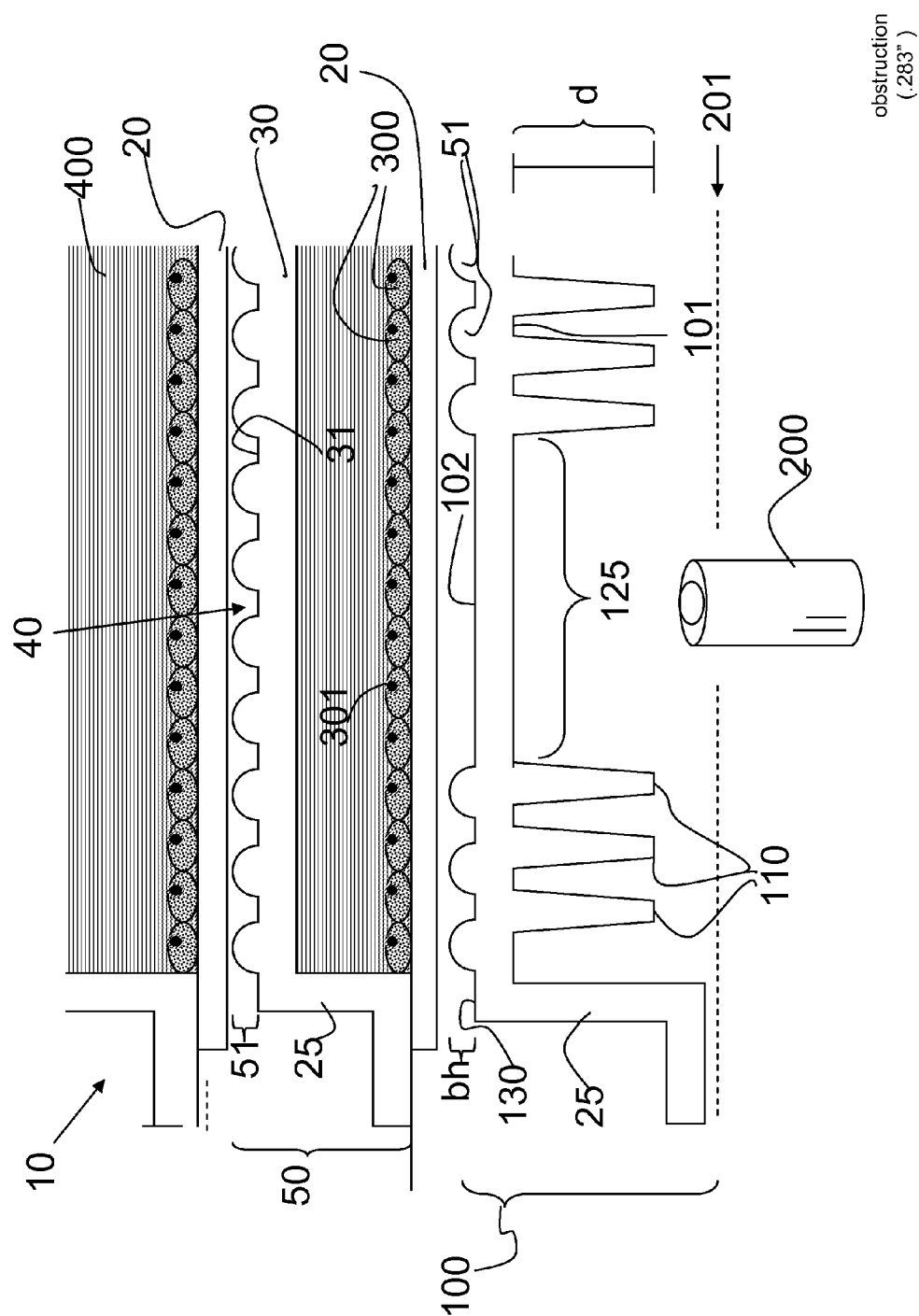
FIG. 3 is a drawing illustrating an embodiment of the bottom two cell culture layers of a multi-layer cell culture device, and an embodiment of a bottom plate, structured and arranged to accommodate a microscope lens.

FIG. 3 is a drawing illustrating an embodiment of the bottom two cell culture chambers 50 of a multi-layer cell culture device 10, and an embodiment of a bottom plate 100, structured and arranged to accommodate a microscope lens 200. The bottom plate 100 has supporting ribs 110 extending from a bottom surface 101 of the bottom plate 110 having a depth "d" and a top surface 130 having bumps 51. Bumps 51 have a bump height (bh). Ribs 110 are useful in the molding of the part because they provide uniform wall thicknesses in the molded part so that all areas in the mold fill evenly. In addition, ribs 110 allow for a reduction of use of raw material plastic resin. For example, in the absence of ribs, the depth of the bottom plate 100 could be filled in with resin. In addition, ribs 110 are used to support the device, and to help keep the device from deforming. Ribs 110 keep the bottom of the multi-layer cell culture apparatus from bowing under the weight of multiple layers of cell culture chambers or stackettes filled with cell culture medium.

The bottom plate 100 also has at least one window 125, a space on the bottom surface 101 of the bottom plate 110 without supporting ribs 110. At least one window 125 has a corresponding area 102 on the top surface 130 or top side of the bottom plate 100 free of bumps 51.

In some multi-layer cell culture devices, the thickness of the bottom plate prevents visualization of cells growing on any of the layers with an inverted microscope, because the distance to the cell layers exceeds the working distance of typical lenses in inverted microscopes.

Also shown in FIG. 3 is a microscope lens 200. The microscope lens extends upwardly from a microscope (not shown) toward the multi-layer cell culture apparatus 10. The multi-layer cell culture apparatus 10 sits on the bottom plate on a microscope stage 201. Cells 300 grow in cell culture chambers 50 bathed in cell culture medium 400. Because of the structure of the bottom plate of the multi-layer cell culture apparatus 10, cells 300 (cells are illustrated with nuclei 301) growing in cell culture chambers 50 are far away from the microscope lens of the typical microscope, making visualization of cells in the multi-layer cell culture device difficult. To make visualization of the cells more effective, the window 125 is provided to allow a microscope lens to extend closer to the bottom surface 101 of the bottom plate, and allowing the microscope to focus on the cells 300 in culture. In addition, the removal of bumps 51 from the corresponding area on the top surface 102 or top side of the bottom plate 100, allows the microscope lens 200 to better focus on cells 300 in culture in the multi-layer cell culture apparatus.

Figure 4:
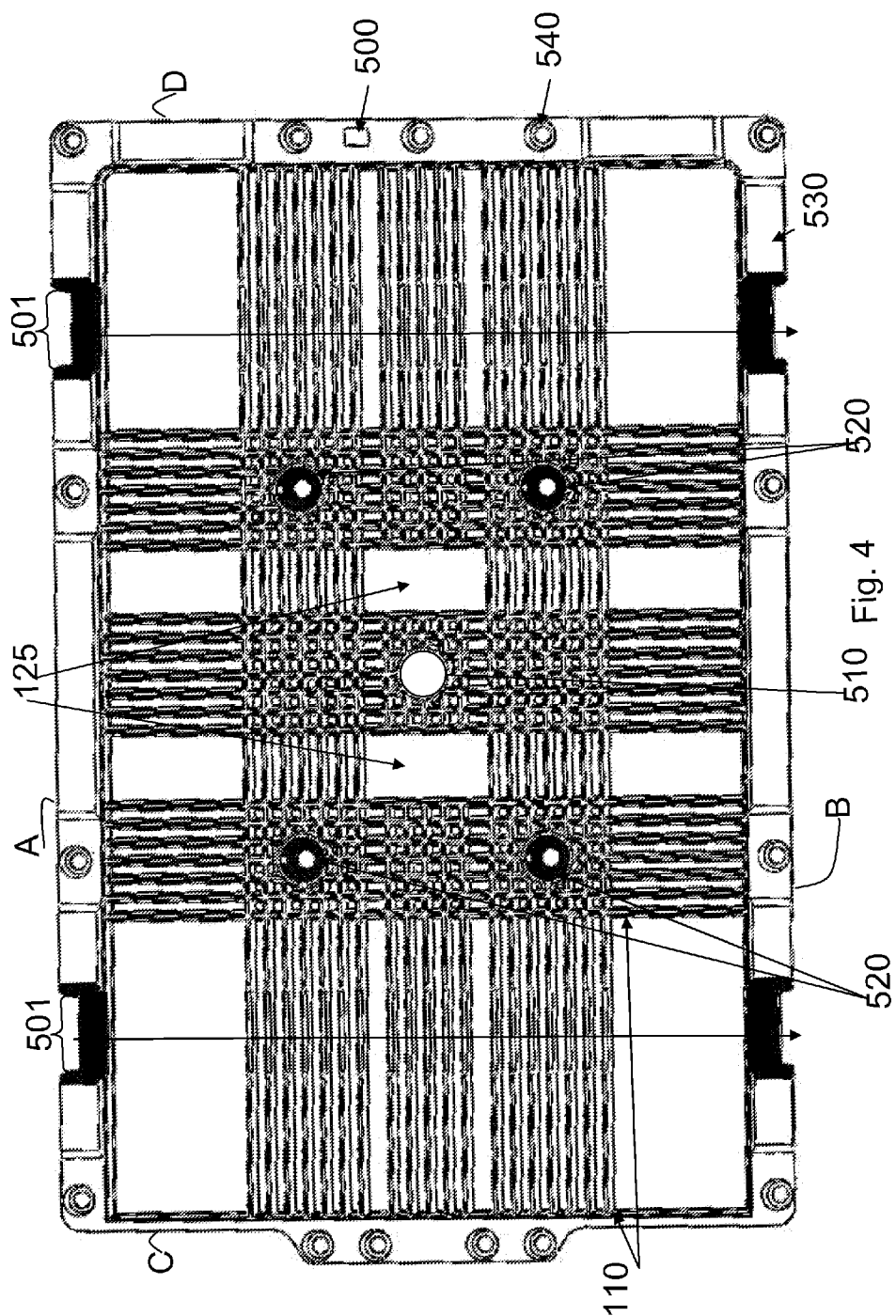
FIG. 4 is a drawing illustrating the bottom surface of an embodiment of a bottom plate of a multi-layer cell culture device.

FIG. 4 is a drawing illustrating the bottom surface of an embodiment of a bottom plate 100 of a multi-layer cell culture device. Support ribs 110 are shown extending from one side A and C to opposite sides B and D of the bottom plate 100. The bottom plate 100 may have lock features to lock the bottom plate to the one multi-layered stack of cell culture chambers to a second stack of multi-layered cell culture chambers. These lock features may be complementary geometric features that allow adjacent parts to engage releasably or permanently with each other. One of these types of connectors is a press-lock 500, a hooked male extension that fits into a complementary female recess on an adjacent part. Or the press-lock can be a rectangular hole which slips over a rectangular cone on a module above or below the bottom plate. Embodiments of lock features include releasable lock features such as the press-lock feature described above, or permanent lock features such as fitted extensions which may be welded into place. Additional lock features may be hook and eye connectors, resealable connections which zip, snap, adhere, or otherwise connect, releasably or permanently. Lock feature may also keep the stack of modules straight and stacked in relationship to one another.

The bottom plate may have strap recesses 501. These strap recesses 501 are cavities structured and arranged to allow a strap, used to bind a storage tray or a carrying tray, or another multi-layer cell culture apparatus to a multi-layer cell culture apparatus. The strap may wrap around the apparatus, seated in the strap recesses 501, as shown by arrows in FIG. 4. The strap recess may also be used to wrap tubing around the multi-layer cell culture apparatus to allow the tubing to engage with the apparatus without being pinched. By recessing straps or tubing in a strap recess, the straps or tubing won't be caught when the vessel is dragged across a surface. Windows 125 are shown in FIG. 4. Although not shown in FIG. 4, there are support bumps everywhere else on the upper surface of the bottom plate that comes in contact with the gas permeable film, but not on the upper surface corresponding to a window area on the top surface 102 or top side of the bottom plate.

Also shown in FIG. 4 is the gate 510. The gate is the area where melted resin flows into a part mold. On the stackette, or cell culture chamber, film may be welded to this spot. As a result, no cell can attach at this point. Rivet holes 520 permit plastic rivets to be put through a group of stackettes or cell culture chambers that together form a multi-layer cell culture apparatus. The film is also welded at these points and a hole is pierced through the center so that there is no leaking when a rivet is pushed through.

The bottom plate may also have feet or pads 530 around the perimeter of the bottom plate. These feet or pads permit stacking of the vessels and prevent the device from catching as the vessel is dragged across a surface.

Additionally, the bottom plate may have bosses 540 where where plastic rivets may be used to keep the individual cell culture chambers or stackettes together in a multi-layer cell culture apparatus. Alternatively, longer plastic rivets may be used in these places to hold together stacks of modules.

Also disclosed herein is a system for visualizing cells in a multi-layer cell culture device comprising the multi-layer cell culture device described above and further comprising a focal point length extender structured and arranged to fit into the at least one window. In embodiments, the focal length extender is made from a high refractive index material. For purposes of this disclosure, "high refractive index material" is optically clear materials with a refractive index greater than 1.45. For example a material with a refractive index (RI) in the range of 1.45 to 2.49 may be considered a high refractive index material. Examples of high refractive index material that is suitable for focal point length extender are, for example fused silica (quartz): RI=1.45, crown glass: RI=1.52, borosilicate glass: RI=1.47, acrylic (PMMA): RI=1.49, polycarbonate: RI=1.58, PET, PETG: RI=1.57, Cubic Zirconia: RI=2.15, diamond: RI=2.42, polystyrene: RI=1.59 (the current prototype is polystyrene), Aluminum oxide (single crystal): RI=1.77, or Titanium dioxide (single crystal): RI=2.49.

FIG. 5 shows an embodiment of a focal length extender 600, which is, in this embodiment, a lens 601. When the bottom plate of the multi-layer cell culture apparatus 10 sits on a microscope stage 201, depending upon the type of microscope used, the lens of the microscope may not extend far enough, and the focal length of the lens may not be long enough, to focus on cells 300 growing on the gas permeable, liquid impermeable membrane 20 in the bottom cell culture chamber or stackette. For example, the depth of the ribs may be, 0.283 inches. The distance from the microscope stage to the cell layer may be 0.437 inches. This is beyond the normal working length of objective lenses in inverted microscopes.

As shown in FIG. 6, in an embodiment, the focal length extender 600 is two commercially available lenses 602 (Edmund Optics Cat. # NT48-175 and NT-48-174 made from high refractive index material (acrylic) which were combined and placed into a window. When the bottom plate of the multi-layer cell culture apparatus 10 sits on a microscope stage 201, depending upon the type of microscope used, the lens of the microscope may not extend far enough to be able to focus on the cells growing on the gas permeable, liquid impermeable membrane in the bottom cell culture chamber or stackette. Using this double-lens focal point length extender 600, the working distance of the microscope objective was extended. The double lenses acted as a bridge between the focal length of the objective lens on the inverted microscope, or a focal length extender, and the lowest cell culture layer. Using the system shown in FIG. 6 allowed the microscope lens to better focus on the plane of the cells, and allowed the multi-layer cell culture device combined with the focal point length extender to better visualize cells in culture.

FIG. 7 is a drawing illustrating an embodiment of the bottom two cell culture layers of a multi-layer cell culture device, and an embodiment of a bottom plate, structured and arranged to accommodate a microscope lens, and also showing an embodiment of a microscope adaptor. FIG. 7 shows an embodiment of the focal point length extender 600, a block of high refractive index material 603. When the bottom plate of the multi-layer cell culture apparatus 10 sits on a microscope stage 201, depending upon the type of microscope used, the lens of the microscope may not extend far enough to be able to focus on the cells growing on the gas permeable, liquid impermeable membrane in the bottom cell culture chamber or stackette. The block of high refractive index material 603 embodiment of the focal point length extender 600 allows the microscope lens to better focus on the plane of the cells, and allows the multi-layer cell culture device combined with the focal point length extender to better visualize cells in culture.

The focal length extender or focal point length extender 600 may be a separate part which is releasably seated into the window or on the microscope stage prior to using the microscope, or the focal point length extender may be sealed or permanently engaged or fitted into the bottom plate. Focal point length extenders of different thickness and curvature may be added or molded into the bottom plate in several locations to permit observation of various layers in the stack.

In embodiments, the height of the cell culture chamber 50 may be, for example 0.194 inches. The height of the tracheal space may be, for example, 0.035 inches. The height of the bumps (bh) may be, for example, from 0.025 to 0.035 inches.

The thickness of the upper plate may be, for example, 0.080 inches. The height from the bottom of the apparatus to the bottom-most layer of cells (h) may be up to 0.5 inches. The height of the ribs (d) may be, for example, 0.1 to 0.5 inches, or from 0.1 to 0.4 inches, or from 0.1 to 0.35 inches or from 0.1 to 0.3 inches. In embodiments, the focal point length extender may be longer than the depth "d" of the support ribs.

In embodiments, the cell culture chamber or stackette bottom is gas permeable material on which cells attach and grow (height=2 mm, 500 $cm^2$/layer, 100 ml/layer, 0.2 ml media/ $cm^2$). Spaces between each stackette, the tracheal chambers, provide equal access for gas exchange (height=0.8 mm). Gases diffuse through the film to meet metabolic needs of cells in culture (film may be, for example, 76.2μ thick).

Multi-layer cell culture systems as disclosed herein may be assembled by any known method. For example, gas permeable liquid impermeable membrane 20 and opposing surfaces 30 can be affixed to side walls 25 by any number of methods including but not limited to adhesive or solvent bonding, heat sealing or welding, compression, ultrasonic welding, laser welding and/or any other method commonly used for generating seals between parts. Laser welding around the circumference of the membrane 20 is preferred to establish a hermetic seal around the membrane region such that the membrane is flush with and fused to the face of the sidewalls 25 such it becomes an integral portion of the interior surface of the multi-layer flask. Once the gas permeable membrane 30 is adhered to the sidewalls, the top plate 30 and bottom plate 100 may be joined. The bottom plate 100 may be injection molded. Various sizes and shapes may be used.

Gas permeable, liquid impermeable membranes 30 may be made of one or more membranes known in the art. Membranes typically are made of suitable materials that may include for example: polystyrene, polyethylene, polycarbonate, polyolefin, ethylene vinyl acetate, polypropylene, polysulfone, polytetrafluoroethylene (PTFE) or compatible fluoropolymer, a silicone rubber or copolymer, poly(styrene-butadiene-styrene) or combinations of these materials. As manufacturing and compatibility for the growth of cells permits, various polymeric materials may be utilized. For its known competency, then, polystyrene may be a preferred material for the membrane (of about 0.003 inches in thickness, though various thicknesses are also permissive of cell growth). As such, the membrane may be of any thickness, preferably between about 25 and 250 microns, but ideally between approximately 25 and 125 microns.

The multi-layer flask 100 of the present invention may be made by any number of acceptable manufacturing methods well known to those of skill in the art. In an embodiment of a method, the multi-layer apparatus 10 is assembled from a collection of separately injection molded parts. Although any polymer (such as polystyrene, polycarbonate, acrylic, polystyrene, or polyester) suitable for molding and commonly utilized in the manufacture of laboratory ware may be used, polystyrene is preferred. Although not required, for optical clarity, it is advantageous to maintain a thickness of no greater than 2 mm. The separate parts may be assembled by any number of methods including but not limited to: adhesive or solvent bonding, heat sealing or welding, compression, ultrasonic welding, laser welding and/or any other method commonly used for generating seals between parts such that it becomes an integral portion of the interior surface of the multi-layer flask. The top plate and bottom plate may be aligned and joined, such as by laser welding.

In an embodiment, parts are held together and are adhesive bonded along the seam, ultrasonically welded, or laser welded, bonded using heat platens or by any other methods. Preferably, laser welding equipment is utilized in a partially or fully automated assembly system. The top plate and tray are properly aligned while a laser weld is made along the outer periphery of the joint.

Advantageously and in order to enhance cell attachment and growth, the surfaces internal to the multi-layer flask 10, including the membrane layer, may be treated to enable cell growth. Treatment may be accomplished by any number of methods known in the art which include plasma discharge, corona discharge, gas plasma discharge, ion bombardment, ionizing radiation, and high intensity UV light.

In an embodiment, the multi-layer flask of the present invention may be manufactured and sterilized.

In a first embodiment, provided is a multi-layer cell culture device comprising at least two cell culture chambers, each cell culture chamber having a gas permeable, a bottom surface formed from liquid impermeable membrane, side walls and an opposing plate forming a top surface, wherein the gas permeable, liquid impermeable membrane forming a bottom surface and the opposing plate are sealed to side walls to form cell culture chambers, wherein the opposing plate has a top side and the top side of the opposing plate has bumps, wherein each cell culture chamber is adjacent to a tracheal space; and, a bottom plate comprising a bottom side having support ribs having a depth "d" and a top side having bumps; wherein the gas permeable, liquid impermeable membrane of each cell culture chamber rests on the bumps on the top side of an opposing plate of an adjacent cell culture chamber or the bottom plate; wherein the bottom plate further comprises at least one window between support ribs; and wherein the top side of the bottom plate opposite the at least one window is free of bumps.

In a second embodiment, the disclosure provides the multi-layer cell culture device of the first embodiment wherein the support ribs extend from one side to an opposite side of the bottom plate.

In a third embodiment, the disclosure provides the multi-layer cell culture device of embodiments 1 or 2, wherein the bottom plate comprises a lock feature.

In a fourth embodiment, the disclosure provides the multi-layer cell culture device of embodiment 3 wherein the lock feature is a press-lock.

In a fifth embodiment, the disclosure provides the multi-layer cell culture device of embodiment 3, wherein the lock feature is a releasable lock.

In a sixth embodiment, the disclosure provides the multi-layer cell culture device of embodiment 3, wherein the lock feature is a permanent lock.

In a seventh embodiment, the disclosure provides the multi-layer cell culture device of any one of embodiments 1-6 wherein the bottom plate comprises strap recesses.

In an eighth embodiment, the disclosure provides the multi-layer cell culture device of any one of embodiments 1-7 wherein the bottom plate comprises rivet holes.

In a ninth embodiment, the disclosure provides the multi-layer cell culture device of any one of embodiments 1-8 wherein the bottom plate comprises feet.

In a tenth embodiment, the disclosure provides the multi-layer cell culture device of any one of embodiments 1-7 wherein the bottom plate comprises bosses.

In an eleventh embodiment, the disclosure provides a system for visualizing cells in a multi-layer cell culture device comprising the multi-layer cell culture device of embodiment 1 and further comprising a focal length extender structured and arranged to fit into the at least one window.

In a twelfth embodiment, the disclosure provides the system of embodiment 11 wherein the focal length extender comprises a lens.

In a thirteenth embodiment, the disclosure provides the system of embodiment 11 or 12 wherein the focal point length extender wherein the focal length extender comprises a double lens.

In a fourteenth embodiment, the disclosure provides the system of any one of embodiments 11-13 wherein the focal point length extender wherein the focal length extender comprises a block of high refractive index material.

In a fifteenth embodiment, the disclosure provides the system of any one of embodiments 11-14 wherein the focal point length extender wherein the focal length extender is longer than the depth "d" of the support ribs.

The invention being thus described, it would be obvious that the same may be varied in many ways by one of ordinary skill in the art having had the benefit of the present disclosure. Such variations are not regarded as a departure from the spirit and scope of the invention, and such modifications as would be obvious to one skilled in the art are intended to be included within the scope of the following claims and their legal equivalents.

The invention claimed is:

1. A multi-layer cell culture device comprising:
at least two cell culture chambers, each cell culture chamber having a gas permeable, liquid impermeable membrane forming a bottom surface, side walls and an opposing plate forming a top surface, wherein the gas permeable, liquid impermeable membrane forming a bottom surface and the opposing plate are sealed to side walls to form cell culture chambers, wherein the opposing plate has a top side and the top side of the opposing plate has bumps, wherein each cell culture chamber is adjacent to a tracheal space; and,
a bottom plate comprising a bottom side having support ribs having a depth "d" and a top side having bumps;
wherein the gas permeable, liquid impermeable membrane of each cell culture chamber rests on the bumps on the top side of an opposing plate of an adjacent cell culture chamber or the bottom plate;
wherein the bottom plate further comprises at least one window between support ribs; and wherein the top side of the bottom plate opposite the at least one window is free of bumps.

2. The multi-layer cell culture device of claim 1 wherein the support ribs extend from one side to an opposite side of the bottom plate.

3. The multi-layer cell culture device of claim 1, wherein the bottom plate comprises a lock feature.

4. The multi-layer cell culture device of claim 2, wherein the bottom plate comprises a lock feature.

5. The multi-layer cell culture device of claim 3 wherein the lock feature is a press-lock.

6. The multi-layer cell culture device of claim 3, wherein the lock feature is a releasable lock.

7. The multi-layer cell culture device of claim 3, wherein the lock feature is a permanent lock.

8. The multi-layer cell culture device of claim 1 wherein the bottom plate comprises strap recesses.

9. The multi-layer cell culture device of claim 1 wherein the bottom plate comprises rivet holes.

10. The multi-layer cell culture device of claim 1 wherein the bottom plate comprises feet.

11. The multi-layer cell culture device of claim 1 wherein the bottom plate comprises bosses.

12. A system for visualizing cells in a multi-layer cell culture device comprising the multi-layer cell culture device of claim 1 and further comprising a focal point length extender structured and arranged to fit into the at least one window.

13. The system of claim 12 wherein the focal point length extender comprises a lens.

14. The system of claim 12 wherein the focal point length extender comprises a double lens.

15. The system of claim 12 wherein the focal point length extender comprises a block of high refractive index material.

16. The system of any claim 12 wherein the focal point length extender is longer than the depth "d" of the support ribs.

17. The system of claim 16 wherein the focal point length extender is longer than the depth "d" of the support ribs.

* * * * *